(12) United States Patent
Bernstein

(10) Patent No.: US 6,552,040 B1
(45) Date of Patent: Apr. 22, 2003

(54) USE OF NITROXIDES IN WOUND HEALING AND IN THE PREVENTION OF PHOTODAMAGE

(76) Inventor: Eric F. Bernstein, 3121 Grennox Rd., Wynnewood, PA (US) 19096

( * ) Notice: Subject to any disclaimer, the term of this patent is extended or adjusted under 35 U.S.C. 154(b) by 0 days.

(21) Appl. No.: 10/018,301
(22) PCT Filed: Jun. 15, 2000
(86) PCT No.: PCT/US00/16374
§ 371 (c)(1),
(2), (4) Date: Apr. 19, 2002
(87) PCT Pub. No.: WO00/78316
PCT Pub. Date: Dec. 28, 2000

Related U.S. Application Data

(60) Provisional application No. 60/140,537, filed on Jun. 23, 1999.

(51) Int. Cl.$^7$ .............................................. A61K 31/445
(52) U.S. Cl. ...................................................... 514/315
(58) Field of Search ......................................... 514/315

(56) References Cited

U.S. PATENT DOCUMENTS

| | | | |
|---|---|---|---|
| 5,462,946 A | 10/1995 | Mitchell et al. | ............. 514/315 |
| 5,840,734 A | 11/1998 | Bernstein | ..................... 514/315 |

Primary Examiner—Raymond Henley, III
(74) Attorney, Agent, or Firm—Licata & Tyrrell P.C.

(57) ABSTRACT

Methods for preventing photoaging and other types of sun damage and promoting wound healing by topically applying a nitroxide containing compound are provided.

7 Claims, No Drawings

USE OF NITROXIDES IN WOUND HEALING AND IN THE PREVENTION OF PHOTODAMAGE

This is a 371 of PCT/US00/16374 filed Jun. 15, 2000 which claims benefit of U.S. Provisional Application No. 60/140,537 filed Jun. 23, 1999.

BACKGROUND OF THE INVENTION

The effects of ultraviolet radiation from exposure to the sun on human skin are a growing concern for today's longer-lived population. The majority of changes associated with an aged appearance result from chronic sun-damage (Warren et al., *J. Am. Acad. Dermatol.*, 1991, 25:751–760; Frances, C. and Robert, L., *Int. J. Dermatol.*, 1984, 23:166–179). Dramatic alterations of the superficial dermis accompany the deep wrinkles and laxity common in photoaged skin. The major histopathologic alteration of photoaged skin is the accumulation of material which, on routine histopathologic examination, has the staining characteristics of elastin and is, thus, termed solar elastosis. Immunohistochemical staining has shown the poorly-formed fibers comprising solar elastosis to be composed of elastin (Chen et al., *J. Invest. Dermatol.*, 1986, 87:334–337; Mera et al., *Br. J. Dermatol.*, 1987, 117:21–27) fibrillin (Chen et al., *J. Invest. Dermatol.*, 1986, 87:334–337; Dahlback et al., *J. Invest. Dermatol.*, 1990, 94:284–291; Bernstein et al., *J. Invest. Dermatol.*, 1994, 103:182–186) and versican, the normal components of elastic fibers (Zimmerman et al., *J. Cell. Biol.*, 1994, 124:817–825). A coordinate increase in elastin, fibrillin and versican mRNAs has been demonstrated in fibroblasts derived from photodamaged skin, as compared to fibroblasts derived from normal skin from the same individuals (Bernstein et al., *J. Invest. Dermatol.*, 1994, 103:182–186). Elevated elastin mRNA levels in sun-damaged skin result from enhanced elastin promoter activity, as shown by transient transfections of fibroblasts with a DNA construct composed of the human elastin promoter linked to the chloramphenicol acetyltransferase (CAT) reporter gene (Bernstein et al., *J. Invest. Dermatol.*, 1994, 103:182–186).

The generation of free radicals following exposure of the skin to ultraviolet radiation is well known in the art. Free radical mechanisms have been shown to be responsible for redness and erythema resulting from exposure to ultraviolet radiation. A number of antioxidants have been tested as photoprotective agents, however, results from these studies indicate that the ability of these agents to provide protection is variable.

Miyachi Y., *J. Dermatol. Sci.* 1995, 9:75–86 provides a review of photoaging from a photo-oxidative standpoint and suggests that use of antioxidants as regulators of photoaging. Specifically studies with superoxide dismutase (SOD) are described. However, it was concluded that sunscreen agents provided better protection from ultraviolet radiation.

Bissett et al. *Photodermatol. Photoimmunol. Photomed.* 1990, 7:56–62 demonstrated that mice, topically treated with solutions of superoxide-scavenging anti-oxidants such as alphatocopherol, ascorbic acid, propyl galate and Trolox prior to ultraviolet B (UVB) radiation exposure, exhibited significantly less damage than untreated mice. However, additional antioxidants or free radical scavengers that were tested, including glutathione, beta-carotene, BHT, mannitol, divinylglycol, pantetheine, urea and histidine, provided no significant protection against UVB radiation. Further, the severity of UVA radiation-induced mouse skin damage was not reduced by topical application of these antioxidants in these studies. Thus, it is clear that the current approaches used to prevent the cumulative effect of photoaging are inadequate.

Historically, more research has been done in the area of radiation oncology. Damage from ionizing radiation and a portion of ultraviolet radiation-induced damage has been shown to be due to the formation of radical oxygen species. Sulfhydryl compounds were among the first radioprotectors to be identified. Their protective mechanism appears to be due to their ability to scavenge radiation-induced free radicals and/or donate reducing equivalents to oxidized molecules. hematopoietic cytokines have also been investigated as radioprotectors. They are believed to protect by more quickly restoring hematopoietic function after radiation exposure.

Recently, a new class of radioprotectors, referred to as nitroxides, has been described. As a class, nitroxides are stable free radical components which react with a variety of biologically relevant compounds including other free radicals (Nilsson et al. *J. Biol. Chem.*, 1989, 264:11131–11135). The observation that several nitroxides themselves reacted with free radicals, specifically oxy radicals, led to the investigation of these compounds as radioprotectors (Saminu et al. *Free Radical Biol. Med.*, 1989, 6:141–148).

Tempol [4-hydroxy-2,2,6,6-tetramethyl-piperidinyloxy, free radical] is a piperindinyl-n-oxyl with the n-oxide sterically stabilized by symmetric pairs of adjacent methyl groups. This compound is commercially available through Aldrich Chemical Co., Milwaukee, Wis. It is most commonly used to spin label biological molecules such as NADP.

Tempol has been demonstrated to function as a superoxide dismutase (SOD) mimic, protecting mammalian cells from superoxide generated from hypoxanthine/xanthine oxidase and from hydrogen peroxide mediated cytotoxicity (Mitchell et al. *Biochem.*, 1990, 29:2802–2807; Samuni et al., *J. Biol. Chem.*, 1988, 263:17921–17924). Tempol has also been demonstrated to provide both in vitro and in vivo protection against ionizing radiation (Mitchell et al. *Arch. Biochem. Biophys.*, 1991, 289:62–70) and to protect against radiation-induced alopecia by speeding the recovery of hair growth within a field of heavily irradiated skin (Goffman et al. *Int. J. Rad. Onc. Biol. Phys.*, 1992, 22:803–806). This protection has been suggested to be linked to direct protection of hair follicle stem cells and development of other nitroxides.

U.S. Pat. No. 5,840,734 describes the use of Tempol in prevention of photoaging, sunburn and skin cancer caused by the UVA and UVB rays of sunlight.

It is now believed that topical application of nitroxide containing compounds other than Tempol will prevent photoaging, and other skin damage resulting from exposure to solar, and more specifically, ultraviolet radiation, such as sunburn and skin cancer. Further, topical application of nitroxide containing compounds is believed to be effective in promoting healing of acute and chronic wounds.

SUMMARY OF THE INVENTION

The present invention relates to a new use for nitroxide containing compounds. It is now believed that topical application of nitroxide containing compounds other than Tempol protects against photodamage including photoaging and other sun-damage such as sunburn and skin cancer caused by solar radiation. Further, it is believed that topical application of nitroxide containing compounds will also promote healing of acute and chronic wounds. Accordingly, nitroxide containing compounds are believed to be useful not only as sunscreen agents but also in wound healing. Thus, the present invention also relates to compositions comprising nitroxide containing compounds for use as sunscreen agents and in wound healing.

DETAILED DESCRIPTION OF THE INVENTION

Nitroxides are stable free radicals with antioxidant catalytic activities similar to superoxide dismutase. Nitroxides existing in vivo have been shown to interact with other substances to also mimic catalase activities. Thus, nitroxide containing compounds have been described in the art for numerous uses. For example, U.S. Pat. No. 5,462,946 discloses biologically compatible compositions containing an effective amount of a metal independent nitroxide compound for use in protecting the skin against ionizing radiation, mucositis, the effects of whole body radiation and radiation induced hair loss. In this embodiment, the nitroxide containing composition is applied topically as an ointment, lotion or cream, intravenously or orally by pill or lozenge. This patent also teaches the nitroxide containing compounds to be useful as protectants against: increased oxygen exposure so as to avoid pulmonary adult respiratory distress syndrome; oxygen-induced lenticular degeneration and hyaline membrane disease in infants; oxidative stress-induced cataracts; reperfusion injury in treating cardiovascular phenomena such as myocardial infarction and strokes, pancreatitis or intestinal ulceration and organ transplant; cytotoxicity due to excess oxidation in animal or plant cell cultures; cytotoxic effects of chemotherapeutic agents; and mutagenic and carcinogenic agents. Also taught in this patent is use of these compounds as anti-inflammatory agents effective against arthritic conditions. In this embodiment, the nitroxide containing compositions are administered parenterally, intra-articularly or via oral ingestion. This patent also teaches use of these compounds as aging retardants when administered orally or parenterally and in weight reduction when administered orally or intravenously.

U.S. Pat. Nos. 5,824,781, 5,840,701 and 5,817,632 teach compositions and processes to alleviate free radical toxicity based on use of nitroxides in association with physiologically compatible macromolecules. These compositions are suggested to be useful as blood substitutes, radioprotective agents, imaging agents, agents to protect against ischemia and reperfusion injury, particularly cerebral stroke, and in vivo enzyme mimics.

It is now believed that topical application of a composition comprising a nitroxide containing compound will be useful not only in protecting against photodamage including photoaging, sunburn and skin cancer but also in the promotion of wound healing. For purposes of the present invention, by "nitroxides" or "nitroxide containing compound" it is meant stable nitroxide free radicals. Examples of nitroxide containing compounds are well known in the art and taught in prior art references such as U.S. Pat. No. 5,462,946. Use of Tempol in compositions for protection against photodamage, including photoaging, sunburn and skin cancer, is specifically excluded from this definition.

Profound changes take place in the superficial dermis as a result of chronic sun-exposure. The major alteration is the deposition of massive amounts of abnormal elastic material, termed solar elastosis. It has been shown that solar elastosis is accompanied by elevations in elastin and fibrillin mRNAs and elastin promoter activity. Various in vivo and in vitro models have been developed which contain a human elastin promoter linked to a reporter gene for evaluating the ability of these compounds to protect against photodamage.

For example, a transgenic mouse line expressing the 5.2 kb human elastin promoter linked to a chloramphenicol acetyltransferase reporter gene (CAT) has been developed which models cutaneous photoaging (Bernstein et al., *J. Invest. Dermatol.*, 1995, 105, 269–273). Although phenotypically normal, the cells in these mice possess the human elastin promoter/CAT construct, allowing elastin promoter activity to be measured in response to stimuli such as ultraviolet radiation (UV). In this model, four or five day old mice which have not yet developed hair, and cell cultures derived from the mice, have been demonstrated to provide a rapid and sensitive means of identifying compounds capable of inhibiting cutaneous photodamage (Bernstein et al., *J. Invest. Dermatol.*, 1995, 105, 269–273; Bernstein et al., *Photochem. Photobiol.*, 1996, 64:369–74; Bernstein et al., *J. Am. Acad. Dermatol.*, 1997, 37:725–729).

A transgenic hairless mouse model has also been developed which permits the investigation of human elastin promoter activity in response to ultraviolet irradiation both in vivo by direct irradiation of mouse skin, and in vitro by irradiation of cells derived from these mice. It is preferred that the hairless mouse used in the production of the transgenic mice for these experiment be of a strain Crl:SKH1-hrBR (Charles River) as this hairless strain of mice is well characterized and used routinely in preclinical dermatological and photobiological research. These transgenic hairless mice of are capable of expressing a full length or truncated elastin promoter. By "truncated human elastin promoter" it is meant a human elastin promoter shorter than the full length 5.2 kb human elastin promoter such as pEP62, pEP35, pEP10, pEP27, and pEP6 (Kahari et al., *J. Biol. Chem.*, 1990, 265(16):9485–9490) which is activated by UV. In a preferred embodiment, the truncated elastin promoter is pEP6. It is also preferred that the promoter be linked to a reporter gene such as the chloramphenicol acetyltransferase reporter gene (CAT) for ease in detecting activity of the full length or truncated promoter.

These models express human elastin promoter activity in a tissue-specific and developmentally regulated manner. Promoter activity can be studied in this model as a function of small increases in ultraviolet radiation, demonstrating the sensitivity of the assay. In addition, quantitative data can be obtained after only a single exposure to ultraviolet radiation.

Accordingly, nitroxide containing compounds such as those described in U.S. Pat. No. 5,462,946, can be applied topically to these transgenic mice to demonstrate their ability to provide protection against UVA and UVB damage to the skin. The transgenic mouse is then exposed to solar radiation. Mice are sacrificed and skin harvested for determination of CAT activity 24 hours after the last phototreatment. The baseline CAT activity of control mice receiving neither radiation nor nitroxide treatment is standardized to a value of one. Relative increases in CAT activity in mice treated with vehicle alone and vehicle plus nitroxide are then determined. Since elastin promoter activation is a primary event in cutaneous aging, these mice represent a mouse model of human photoaging.

Alternatively, the ability of nitroxide containing compounds to protect against photodamage and/or oxidative damage can be demonstrated in cells stably or transiently transfected with an elastin promoter. In one embodiment, these cells are derived from transgenic mice capable of expressing a full length or truncated human elastin promoter. Alternatively, the cells may be derived from immortalized cell lines. In these experiments, the cells are treated with the nitroxide containing compound. The treated cells are then exposed to solar simulating, UVB or UVA radiation and human elastin promoter activity in the cells is determined. Addition of 8-methoxypsoralen prior to UVA exposure may be required in some cell culture experiments to achieve a significant increase in elastin promoter activity. The activity is then compared to control cells exposed to the same dose of solar simulating, UVB or UVA radiation but which were not treated with the nitroxide containing compound to demonstrate the ability of the nitroxide containing compound to provide protection against the exposure.

Incorporation of a means for generating reactive oxygen species such as a hypoxanthine and xanthine oxidase system within these cell cultures provides a sensitive system for demonstrating the ability of the nitroxide containing compounds to prevent oxidative damage. In these experiments, nitroxide containing compounds are added to the cell cultures prior to addition of the means for generation of reactive oxygen species. The means for generating reactive oxygen species is then added and human elastin promoter activity is determined in the culture after a selected time period. The time period for determination of human elastin promoter can be selected in accordance with routine experiments wherein optimum time span for incubation of cells with a hypoxanthine and xanthine oxidase system is determined. More specifically, optimum time span for incubation is determined by exposing cells to a hypoxanthine and xanthine oxidase system for increasing amounts of time, and determining promoter activity at various times throughout a 24 hour incubation. Optimum time is determined as the point at which CAT activity peaks. Nitroxide containing compounds should provide protection against oxidative damage. Such protection is demonstrated in this assay by a decrease in elastin promoter activity in the cells exposed to the compound and the means for generating reactive oxygen species as compared to control cells.

It is believed that topical application of a composition comprising a nitroxide containing compound is also useful in wound healing. The ability of nitroxide containing compounds to promote wound healing can be demonstrated in well-established wound healing animal models such as the guinea pig model described in Bernstein et al. *J. Dermatologic Surgery and Oncology* 1993, 19(6):564–570 and Bernstein et al. *J. Invest. Dermatol.* 1991, 97:430–434. In these experiments, a composition comprising a nitroxide containing compound can be topically applied to an irradiated skin flap wound of a guinea pig. The ability of the composition to enhance tensile strength, also referred to as wound bursting strength, as compared to animals not receiving the treatment, is then demonstrated after approximately 7 days of healing.

Thus, compositions comprising a nitroxide containing compound are expected to be useful when applied topically as sunscreen agents and in promoting wound healing. Examples of topically applied compositions comprising a nitroxide containing compound include, but are not limited to creams, lotions and sprays. Methods of formulating nitroxide containing compounds into creams, lotions and sprays, as well as pharmaceutical additives for such formulations, are well known to those skilled in the art. As will be obvious to those skilled in the art upon this disclosure, such compositions may further comprise secondary or additional sunscreens, free radical scavengers such as, but not limited to, Vitamin C and Vitamin E and analogs thereof, anti-inflammatory agents, or additional wound healing agents. When used as a sunscreen, it is preferred that the composition be applied to the skin prior to exposure to the sun. However, application of these compositions subsequent to the exposure can also mitigate any damage resulting to the skin from this exposure. It is believed that these compositions of the present invention will be especially useful in protecting individuals with heightened sensitivities to the sun, such as, but not limited to, individuals undergoing psoralen treatment for cancer, psoriasis and other skin conditions; individuals undergoing photodynamic therapy for skin cancer, psoriasis and other skin conditions; individuals suffering from genetic repair defects such as xeroderma pigmentosa, albinism or other conditions resulting from decreased endogenous melanin pigment. When used in wound healing, it is preferred that the composition be applied directly to the wound.

The following nonlimiting examples are provided to further illustrate the present invention.

EXAMPLES

Example 1

Transgenic Mice Expressing the Human Elastin Promoter

A homozygous line of transgenic mice expressing the 5.2-kb human elastin promoter linked to a CAT reporter gene can be used. Hsu-Wong et al., *J. Biol. Chem.*, 1994, 269:18072–18075. These mice express the human elastin promoter in a tissue-specific and developmentally regulated manner. Mice four or five days old must be used since at this age, visible hair growth is not yet present.

Alternatively, a homozygous line of hairless transgenic mice of the strain Crl:SKH1-hrBR (Charles River) expressing either the full length 5.2-kb human elastin promoter linked to a CAT reporter gene or the truncated human elastin promoter, pEP6 (Kahari et al., *J. Biol. Chem.*, 265(16):9485–9490, 1990), linked to a CAT reporter gene can be used.

Example 2

Solar Simulating Radiation

A Multiport Solar Simulator (Solar Light Company, Philadelphia, Pa.) containing a xenon arc lamp filtered through a Schott WG 320 filter (Schott Glaswerke, Mainz, Germany) is used to administer solar simulating radiation (SSR). The output of the solar simulator is measured by means of a 3D UV meter (Solar Light Company) and displayed as human minimal erythema doses (MEDs). The emission spectrum of the lamp closely simulates solar radiation reaching the earth's surface. The light guides from the solar simulator are placed in light contact with the dorsal surface of the mice, which were restrained to prevent movement while SSR is administered. Unirradiated control mice are also restrained without receiving SSR.

Example 3

CAT Assay

To measure the expression of the human elastin promoter/CAT reporter gene construct in the skin of transgenic mice and in cell cultures established from these animals, CAT activity is determined. For extraction of the CAT from skin, the specimens are homogenized in 0.25 Tris-HCl, pH 7.5, using a tissue homogenizer (Brinkmann Instruments, Inc. Westbury, N.Y.). The homogenates are centrifuged at 10,000×g for 15 minutes at 4° C. and the protein concentration in the supernatant determined by a commercial protein assay kit (Bio-Rad Laboratories, Richmond, Calif.). Aliquots of the supernatant containing 100 μg of protein are used for assay of CAT activity by incubation with [$^{14}$C] chloramphenicol in accordance with well-known procedures. The acetylated and non-acetylated forms of radioactive chloramphenicol are separated by thin-layer chromatography and CAT activity is determined by the radioactivity in the acetylated forms as a percent of the total radioactivity in each sample.

Example 4

Impaired Wound Healing Model

Adult female Hartley guinea pigs (400–550 g) are anesthetized with ketamine hydrochloride (90 mg/kg) and xylazine hydrochloride (5 mg/kg) administered intraperitoneally, and then shaved. A skin fold is isolated using a plexiglass box with a slit through which a fold of skin is pulled and secured with 2 clamps. Clamps are placed well outside the area of skin to be incised. The skin fold is placed within the irradiation treatment field, while the remainder of the animal is outside the treatment beam. Shielding against whole body irradiation mimics the clinical setting and prevents possible depletion of bone marrow-derived elements, which may be essential for the healing response to be affected by administration of the nitroxide. A 1 cm thick plexiglass bolus is placed over treated skin to ensure skin dosing on the surface as well as at depth. Guinea pigs are irradiated to treatment sites on one flank to 15 Gy using 4 MeV x-rays delivered by a 4 MeV linear accelerator (SHM Nuclear. Corporation, Sunnyvale, Calif.) at a dose rate of 2.4 Gy/min. This dose has been demonstrated to produce 50% impairment in wound strength over control wounds at 14 days (Gorodetsky et al. *Radiat. Res.* 1988, 115:135–144). Irradiation is carried out 2 days before wounding because this interval has been demonstrated to result in the most significant wound impairment over any other interval up to 3 weeks prior to wounding (Gorodetsky et al. *Radiat. Res.* 1988, 115:135–144).

Treatment sites are selected so that the center of the irradiated fold is 3.5 cm lateral to the midline. On the opposite side of each guinea pig, a skin fold is isolated and clamped in the same manner as the irradiated skin fold, but receives no irradiation. This serves as a control. Paired 5 cm linear incisions are made in each treatment area 3.5 cm from the midline with a scalpel blade. Incisions are closed with 6 Accustaple model 40R stainless steel surgical staples (Deknatel, Queens Village, N.Y.) per incision. Seven guinea pigs are used, each receiving an incision in irradiated and non-irradiated skin. After wounding, guinea pigs are individually housed to prevent them from tampering with each other's treatment sites.

Guinea pigs are killed with sodium pentothol overdose 7 days after wounding. Wounds are evaluated 7 days after wounding since this is the earliest time they are strong enough to permit evaluation by WBS analysis. A flap is raised and skin removed in treatment areas. Then using a hand operated press and sharpened steel template, a 1 cm wide strip of wound is removed from the center of each incision site. Each strip has 1.5 cm of normal tissue on either side of the wound to allow tissue to be secured during wound bursting strength determination. Wound strips are placed in phosphate buffered saline immediately after cutting, and bursting strength determination is carried out within 3 hours after removal. Bursting strength is measured on an Instron 1102 TMS materials tester (Instron Corporation, Canton, Mass.). Strips are subjected to uniaxial extension using a cross speed of 25 cm/minute. Wound bursting strengths are evaluated by subjecting paired values to a t-test analysis (StatWorks, Cricket Software, Inc., Philadelphia, Pa.).

Example 5

Nitroxide Treated Wounds

Skin flaps are irradiated as described in Example 4 with both flaps on each animal receiving irradiation. Incisions are made as above and the nitroxide containing compound is then applied topically to the wound. Control wounds receive no treatment or vehicle alone. After application of the compound, wounds are closed. The skin is harvested after 7 days and wounding and tensile strengths are measured as described in Example 4. Wound bursting strengths are evaluated by subjecting paired or unpaired values to a t-test analysis (StatWorks, Cricket Software, Inc., Philadelphia, Pa.).

What is claimed:

1. A method of protecting humans exposed to sunlight against photodamage comprising topically applying to skin of a human a nitroxide containing compound in an amount effective to protect the skin against photodamage with the proviso that the nitroxide containing compound does not comprise Tempol.

2. The method of claim 1 wherein the nitroxide containing compound is applied prior to exposure of the skin to sunlight.

3. The method of claim 1 wherein the nitroxide containing compound is applied subsequent to exposure of the skin to sunlight.

4. A method of protecting individuals with a heightened sensitivity to the sun from damage resulting from the sun comprising topically applying to the skin of an individual with a heightened sensitivity to the sun a nitroxide containing compound prior to exposure of the individual to the sun, with the proviso that the nitroxide containing compound does not comprise Tempol.

5. A pharmaceutical composition for prevention of photoaging and other sun-damage comprising a nitroxide containing compound, a second sunscreen or free radical scavenger, and a pharmaceutical additive, with the proviso that the nitroxide containing compound does not comprise Tempol.

6. A method of promoting wound healing in a patient comprising topically applying to the wound of a patient a nitroxide containing compound.

7. The method of claim 6 wherein the wound is an acute wound or a chronic wound.

* * * * *